United States Patent [19]

Slife

[11] Patent Number: 4,517,009

[45] Date of Patent: May 14, 1985

[54] HERBICIDAL MIXTURES

[75] Inventor: Fred W. Slife, Urbana, Ill.

[73] Assignee: FBC Limited, Cambridge, England

[21] Appl. No.: 480,576

[22] Filed: Mar. 30, 1983

Related U.S. Application Data

[63] Continuation-in-part of Ser. No. 225,099, Jan. 14, 1981, abandoned.

[30] Foreign Application Priority Data

Jan. 15, 1980 [GB] United Kingdom ................. 8001228

[51] Int. Cl.$^3$ ............................................. A01N 43/78
[52] U.S. Cl. ........................................... 71/90; 71/116
[58] Field of Search ................................... 71/90, 116

[56] References Cited

U.S. PATENT DOCUMENTS 4,032,320  6/1977  Lush ........................................ 71/90
4,063,929 12/1977  Bayer et al. ........................... 71/115

OTHER PUBLICATIONS

Walker et al., Chem. Abst., vol. 96, (1982), 157224f.

Primary Examiner—Catherine L. Mills
Attorney, Agent, or Firm—Gordon W. Hueschen

[57] ABSTRACT

A herbicidal composition useful in controlling weeds comprising benazolin and acifluorfen.

2 Claims, No Drawings

HERBICIDAL MIXTURES

This application is a continuation-in-part of application Ser. No. 225,099 filed 14th Jan. 1981, now abandoned.

This invention relates to herbicidal compositions and to a method of selectively controlling weeds in crops.

Benazolin is the common name for a herbicide having the chemical name 4-chloro-2-oxobenzothiazolin-3-ylacetic acid. In this specification this name is used to mean benazolin as the free acid or one of its salt or ester derivatives acceptable in herbicidal applications.

It has now been found according to the invention, that under certain circumstances synergism is exhibited when benazolin is mixed with acifluorfen.

Since weeds compete with the crop, destruction of all or some of the weeds will usually increase the yield of the crop, unless the herbicide causes too much damage to the crop. We have found that the yield of, for example, soybeans is greater when the mixture is used for weed control than the individual components.

The invention comprises a herbicidal composition comprising benazolin in admixture with acifluorfen.

Acifluorfen is the common name for 5-(2-chloro-4-(trifluoromethyl)phenoxy)-2-nitrobenzoic acid and this name is used to mean the free acid, salts (especially the sodium salt) and ester derivatives.

The invention is generally applicable in controlling weeds in the presence of growing crops such as cereals e.g. corn (*Zea mays*) and in legumes e.g. beans, peanuts and particularly soybeans. The mixtures are preferably applied after the emergence of the weeds when the crop is at an early vegetative stage of growth. Examples of weeds that may be controlled include cocklebur, (*Xanthium spp.*) velvet leaf, (*Abutilon theophrasti*) giant ragweed, (*Ambrosia trifida*), spiny sida (*Sida spinosa*) and various grasses.

The ratio of benazolin to the acifluorfen in the mixture of the invention is preferably within the range of from 10:1 to 1:10, preferably 5:1 to 1:5, e.g. 2:1 to 1:4 the ratios being based on the weight of the two components expressed in terms of the free acid. A suitable application rate expressed in terms of the combined quantity of the two active components (as free acid) is often in the range of from 5 to 50 oz/acre. As examples of the quantities that are most suitable, the rate of application of benazolin can be from 0.5 to 16 e.g. 1 to 8 oz/acre.

The mixture of active herbicides can be applied by, for example a spray treatment in any form known in the art for the formulation of herbicidal compounds and preferably as a dispersion, an aqueous emulsion or an aqueous concentrate.

As a dispersion, the mixture comprises the active components dispersed in a liquid medium, preferably water. The primary composition for a dispersion can be provided in a number of forms. For example it can be a dispersible solution which comprises the active components dissolved in a water-miscible solvent with the addition of a dispersing agent or it can be a dispersible powder comprising the active components and a dispersing agent. A further alternative comprises the active components in the form of a finely ground powder in association with a dispersing agent and intimately mixed with water to give a paste or cream which can if desired be added to an emulsion of oil in water to give a dispersion of active components in an aqueous oil emulsion.

An emulsion comprises the active components dissolved in a water-immiscible solvent which is formed into an emulsion with water in the presence of an emulsifying agent. An emulsion of the desired concentration can be formed from a primary composition of the following types: a concentrated stock-emulsion comprising the active components in combination with an emulsifying agent, water and water-immiscible solvent, or an emulsifiable concentrate comprising a solution of the active components in a water-immiscible solvent containing an emulsifying agent.

The preferred formulation is an aqueous concentrate of the components in a water soluble form, usually salt, dissolved in water and also containing a surfactant.

The above herbicidal formulations are to be regarded as part of the invention. The total concentration of the active components in a composition for direct application to the crop by conventional ground methods is preferably within the range of 0.02 to 10 percent by weight, especially 0.05 to 1 percent by weight, of the composition, but more concentrated compositions containing, for example up to 20 percent may be desirable.

In a primary composition the total amount of active compound can vary widely, for example, from 5 to 95 percent by weight.

The invention is illustrated in the following example.

EXAMPLE

Fields of soybeans, infested with various weeds, were divided into replicate areas and then sprayed at various application rates with aqueous solutions of active ingredients alone and in admixture.

Various tests were carried out at various times and on various sites. Synergism was observed against various weeds as shown in the following results. In some cases the benazolin was used as the ethyl ester (EE), and in others as the dimethylamine salt (DMA). The acifluorfen was used as the sodium salt (AF).

| Treatment | Rate oz/acre | % Kill |
|---|---|---|
| TRIAL 1 | | |
| Cocklebur (*Xanthium spp*). Assessment - 18 days after spraying | | |
| Benazolin (DMA) | 8 | 48 |
| AF | 8 | 25 |
| Benazolin (DMA) + AF | 4 + 4 | 58 |
| TRIAL 2 | | |
| Cocklebur (*Xanthium spp*). Assessment - 21 days after spraying | | |
| Benazolin (DMA) | 6 | 68 |
| AF | 8 | 88 |
| Benazolin (DMA) + AF | 2 + 4 | 95 |
| TRIAL 3 | | |
| Spiny sida (*Sida spinosa*). Assessment - 18 days after spraying. | | |
| Benazolin (EE) | 8 | 0 |
| AF | 8 | 0 |
| Benazolin (EE) + AF | 4 + 4 | 40 |

In some trials Soybeans infested with weeds were treated as previously described. The yield of crop was measured and compared with untreated controls. In the results shown below the mixtures gave greater yield increase of soybeans than the individual components at a rate equal to or less than rate of either of the individual components.

| Treatment | Rate oz/acre | Yield increase (%) |
|---|---|---|
| TRIAL A | | |
| Benazolin (EE) | 8 | 0 |
| AF | 8 | 12 |
| Benazolin (EE) + AF | 4 + 2 | 24 |
| TRIAL B | | |
| Benazolin (DMA) | 6 | 28 |
| AF (DMA) | 6 | 37 |
| Benazolin + AF | 2 + 4 | 47 |
| TRIAL C | | |
| Benazolin (EE) | 8 | 0 |
| AF | 8 | 0 |
| Benazolin (EE) + AF | 4 + 4 | 8 |

What is claimed is:

1. A herbicidal composition, the active components of which consist essentially of a herbicidally-effective amount of benazolin and acifluorfen in a synergistic proportion of benazolin to acifluorfen from 2:1 to 1:2 based upon the weight of the active components expressed as the free acid.

2. A method for the control of weeds after their emergence which comprises applying to the crop area a herbicidally-effective amount of a mixture, the active components of which consist essentially of benazolin and acifluorfen in a synergistic proportion of benazolin to acifluorfen from 2:1 to 1:2 based upon the weight of the active components expressed as the free acid.

* * * * *